United States Patent [19]
Hamilton et al.

[11] Patent Number: 5,978,693
[45] Date of Patent: Nov. 2, 1999

[54] APPARATUS AND METHOD FOR REDUCTION OF MOTION ARTIFACT

[75] Inventors: Patrick S. Hamilton, Newton; Michael G. Curley; Roberto M. Aimi, both of Cambridge, all of Mass.

[73] Assignee: E.P. Limited, Cambridge, Mass.

[21] Appl. No.: 09/017,536

[22] Filed: Feb. 2, 1998

[51] Int. Cl.[6] ............. A61B 5/0402; A61B 5/0448; A61B 5/0478

[52] U.S. Cl. ............. 600/391; 600/394; 600/509; 600/523; 600/544; 600/546

[58] Field of Search .................. 600/372, 386, 600/391, 392, 394, 395, 509, 523, 544, 546

[56] References Cited

U.S. PATENT DOCUMENTS

| | | | |
|---|---|---|---|
| 3,977,392 | 8/1976 | Manley | 128/2.1 E |
| 4,209,020 | 6/1980 | Nielsen | 128/640 |
| 4,274,419 | 6/1981 | Tam et al. | 128/639 |
| 4,503,860 | 3/1985 | Sams et al. | 128/639 |
| 4,708,019 | 11/1987 | Rubner et al. | 73/760 |
| 4,757,817 | 7/1988 | Healy | 128/641 |
| 5,109,842 | 5/1992 | Adinolfi | 128/419 D |
| 5,199,432 | 4/1993 | Quedens et al. | 128/642 |
| 5,247,945 | 9/1993 | Heinze et al. | 607/152 |
| 5,321,257 | 6/1994 | Danisch | 250/277.16 |
| 5,355,883 | 10/1994 | Ascher | 128/641 |
| 5,445,537 | 8/1995 | Abyzov | 439/449 |
| 5,633,494 | 5/1997 | Danisch | 250/227.16 |

OTHER PUBLICATIONS

"Advanced Digital Signal Processing", John G. Proakis, Charles M. Rader, Fuyun Ling, & Chrysostomos L. Nikias, Macmillan Publishing, New York, pp. 337–395, 1992.

"Adaptive Noise Cancelling: Principles and Applications". Widrow, Glover Jr., McCool, Kauntiz, Williams, Hearn, Zeidler, Dong Jr., & Goodlin, Proceedings of the IEEE, vol. 63, pp. 1692–1716, 1975.

"Detecting Electrode Motion Noise in ECG Signals by Monitoring Electrode Impedance", Philip H. Devlin, Roger G. Mark, & John W. Ketchum, Computers in Cardiology, pp. 51–56, 1984.

*Primary Examiner*—Lee Cohen
*Attorney, Agent, or Firm*—Michael J. Weins; Jeffrey E. Semprebon

[57] ABSTRACT

A skin-mounted physiological recording electrode assembly has a foam pad having a front surface having a central recess and mounted to the skin, and a rear surface. A pad passage extends from the central recess to the rear surface. An electrode in the pad passage has a sensing end in the central recess and a connector end to which a clip attaches. The clip attaches to a lead wire connecting to a monitoring device. At least one deformation gauge is coupled to the rear surface of the foam pad, and may be a strain gauge, a bending sensor, or a combination of both. The electrode assembly may be used in a patient monitoring system having an electrode signal processor, sensor signal processors, a multiplexer, an A-to-D convertor, and a microprocessor programmed with an adaptive noise canceling algorithm. A method is taught of monitoring signals from at least two electrodes, generating and monitoring deformation signals which are correlated to the deformation of the foam pads, and making an adaptive noise canceling analysis of the electrode signals and the deformation signals to reduce or eliminate the noise component of the electrode signals.

25 Claims, 6 Drawing Sheets

APPARATUS AND METHOD FOR REDUCTION OF MOTION ARTIFACT

FIELD OF THE INVENTION

The present invention is for an electrode assembly for mounting to the skin of a patient, and particularly for an electrode assembly for use in monitoring and recording physiological data such as electrocardiograms (ECG), electroencephalograms (EEG), and electromyograms (EMG).

BACKGROUND OF THE INVENTION

Motion artifact resulting from electrode and patient movement is a significant source of noise in making physiological recordings such as electrocardiograms (ECG), electroencephalograms (EEG), and electromyograms (EMG). This noise results in a contaminated signal being received from the electrode, and is particularly a problem in cases where it is necessary to make such recordings while the patient is engaged in activity. These artifacts arise from skin deformation which may be produced by forces transmitted through the skin-electrode interface or by forces on the skin generated by movement of the patient.

One approach taught in U.S. Pat. Nos. 4,503,860; 4,757,817; and 5,445,537 to limit such artifacts has been to provide means for anchoring a lead wire connecting the electrode to a recording device being used to make the recording. The anchor absorbs strains on the lead wire due to motion of the patient relative to the recording device and due to the weight and inertia of the lead wire as the patient moves, thus preventing these strains from being transmitted to the electrode itself. While such anchors minimize strains resulting from the lead wire, they do not address strains due to stretching and bending of the skin of the patient.

U.S. Pat. No. 5,355,883 teaches an electrode connector which incorporates a strain gauge. The strain gauge is accommodated in a protective cap of the connector, between a contact member which connects to the electrode and an interior region of the cap. The intent of the '883 device is to generate a strain signal from the strain gauge and subtract the strain signal from the contaminated signal received from the electrode to generate an uncontaminated signal. However, the '883 device only addresses strains experienced by the connector, and does not provide an index based upon the state of deformation of the skin where the electrode is positioned, which can effect the output signal from the electrode. Also, the '883 patent does not teach a method for processing the signals from the strain gauge to provide appropriate weighting of the strain signal with respect to the signal received from the electrode.

Thus, there is a need for a skin-mounted physiological recording electrode assembly which allows for measuring deformation of the skin to which the electrode assembly is mounted, and there is a need for a system which uses such electrode assemblies to remove motion artifacts from a contaminated signal received from the electrodes.

SUMMARY OF THE INVENTION

The present invention relates to a skin-mounted physiological recording electrode assembly and, more particularly, to a skin-mounted physiological recording electrode assembly to reduce the artifacts that are generated by deformation of the skin. This skin deformation is of two types. The skin can deform due to forces in the plane of the skin, hereinafter referred to as skin stretch, and the skin can deform due to forces normal to the plane of the skin, hereinafter referred to as skin normal distortion. The skin-mounted physiological recording electrode assembly of the present invention includes many of the components of conventional skin-mounted physiological electrodes.

The skin-mounted physiological recording electrode assembly has a skin compliant pad, frequently having a circular cross section. The skin compliant pad may be constructed of any material which readily conforms to the local shape of the skin and has a modulus of elasticity similar to that of skin. These pads are frequently referred to as foam pads, and will hereafter be referred to as foam pads. The foam pad has a front surface which engages the skin and a rear surface. The front surface has a central region which is recessed, forming a central recess in the front surface of the foam pad. A pad passage is provided between the central recess and the rear surface of the foam pad. The front surface of the foam pad is placed on the skin of a patient and is maintained on the skin with an adhesive.

The skin-mounted physiological recording electrode assembly has an electrode having a sensing end and a connector end. The electrode passes through the pad passage and is positioned such that the sensing end resides in the central recess. Having the electrode so positioned places the sensing end of the electrode in close proximity to the skin when the foam pad is in contact with the skin. The central recess is typically filled with a conductive paste to provide a conductive path between the skin and the sensing end of the electrode, as is well known in the art. The connector end of the electrode extends beyond the pad passage and beyond the rear surface of the foam pad, making it accessible to a clip which attaches to the connector end of the electrode. The clip in turn is attached to a lead wire which connects to a patient monitoring device.

One aspect of the present invention resides in providing at least one deformation gauge which is coupled to the foam pad. The coupling can be by mechanical attachment with fasteners, such as barbs attached to the deformation gauge and imbedded in the foam pad, by bonding the deformation gauge to the rear surface of the foam pad with an adhesive, or by embedding the deformation gauge in the foam pad. A strain gauge or a bending sensor, or a combination of both, can be employed as the one or more deformation gauges.

Strain gauges are effective in measuring skin stretch. While a single strain gauge can be employed to determine the skin stretch component of the skin deformation, a first strain gauge in combination with a second strain gauge is preferred to measure skin stretch. When the second strain gauge is employed, it is preferably mounted so as to measure strains in a direction substantially normal to direction of strains measured by the first strain gauge.

When resistance strain gauges are employed, they are attached to or embedded in the foam pad and provide a strain signal resulting from the change in resistance as the length of the strain gauge changes. Selection of a resistance strain gauge with an appropriate strain dependence is important to maintain sufficient sensitivity of the strain gauge to the stretching of the skin to produce a strain dependent signal which can be readily measured when the strain gauge is coupled to the foam pad. Since the foam pads have a low modulus of elasticity which matches the modulus of elasticity of the skin, classic foil strain gauges, which rely on a change in the resistance of the foil imbedded therein, will frequently have an effective modulus of elasticity which is high relative to the modulus of elasticity of the foam pad, making it difficult to adequately detect the strain experienced by the foam pad and the underlying skin. For this reason, it is preferred to employ strain gauges which are constructed from a conductive foam which has a strain dependent resistance.

A conductive foam can be selected for the strain gauge which has a modulus of elasticity similar to that of the foam pad, making the strain gauge more responsive to skin stretching. When a conductive foam is employed for the strain gauge, the conductive foam can be embedded in and made an integral part of the foam pad. When the strain gauge is fabricated from conductive foam, it has a first strain gauge end section and a second strain gauge end section. A gauge lead wire connects to strain gauge leads which are connected to the first strain gauge end section and the second strain gauge end section to allow monitoring the change in resistance of the conductive foam of the strain gauge as it is strained due to skin stretch.

One preferred embodiment for a strain gauge which is particularly well suited to provide strain signals for skin stretching is to employ a flexible element having a first attachment region and a second attachment region which are both attached to the foam pad and are separated by a curved unbonded region. As the skin stretches and the foam pad is strained, the change in curvature of the curved unbonded region of the flexible element can be measured to determine the strain in the foam pad. When an optical bending sensor, such as the sensors taught in U.S. Pat. No. 5,321,257 or U.S. Pat. No. 5,633,494, is employed as the flexible element, the change in curvature can be optically monitored to provide a signal which correlates to the strain in the foam pad.

In addition to using bending sensors as discussed above to measure skin stretch, bending sensors can be employed to measure skin normal distortion. When optical bending sensors are employed to measure normal distortion of the skin, they have a central region which is attached to the foam pad, preferably by being bonded thereto. Preferably, this bonded central region of the bending sensor is substantially its full length. When the bending sensor is coupled to the foam pad and the foam pad is attached to the skin, the bending sensor will provide a normal distortion signal which will be a function of the normal distortion of the skin.

Skin normal distortion can also be sensed by employing a frame, to which is attached a resilient strip, rather than employing an optical bending sensor. The frame has a central open region, and rests on a peripheral region of the foam pad. The resilient strip spans the central open region of the frame and has a strip passage therethrough to accommodate the electrode. It should be appreciated that the frame and the resilient strip can be constructed as a single unit.

When a resilient strip is employed, one or more strain gauges are mounted thereon to monitor bending of the resilient strip. The resilient strip is preferably fabricated from a thin sheet of a material such as metal, providing a strip top surface and a strip bottom surface onto which two pairs of strain gauges are attached, thereby providing the analysis needed to monitor the bending. The clip which connects to the connector end of the electrode is so configured that, when it is engaged with the connector end, it serves as means for bending the resilient strip and forcibly engaging the frame with the foam pad to minimize motion between the frame and the foam pad.

The skin-mounted physiological recording electrode assembly has particular utility when it is incorporated into a patient monitoring system which employs at least one pair of skin-mounted physiological recording electrode assemblies having electrodes for monitoring physiological signals, such as the electrode assemblies described above. These electrode assemblies each include at least one deformation gauge coupled to the foam pad for the generation of deformation signals.

The patient monitoring system has an electrode signal processor which receives the physiological signals from the electrodes for each of the at least one pair of physiological recording electrode assemblies and generates amplified differential physiological signals. A deformation signal processor is provided for each deformation gauge to provide processed deformation signals. A multiplexer is provided which selectively passes the amplified differential physiological signals and the processed deformation signals to an A-to-D convertor, which in turn digitizes the signals received to provide digital differential physiological signals and digital deformation signals.

A microprocessor is provided which receives these digital signals. The microprocessor provides adaptive filtering of the signals it receives and is programmed with an adaptive noise canceling algorithm, employing one of the commonly known algorithms such as Least Means Squared (LMS), Recursive Least Square (RLS), and Lattice algorithms. With the aid of these algorithms, the microprocessor combines the digital differential physiological signals and the digital deformation signals to provide filtered digital physiological signals. Further discussion of adaptive filtering algorithms is found in *Advanced Digital Signal Processing* by Proakis, Rader, Ling, Nikias (Macmillan Publishing, New York, 1992) and is described in a paper entitled: "Adaptive Noise Canceling: Principals and Applications", B. Widrow, J. R. Glover Jr., J. M. McCool, J. Kaunitz, C. S. Williams, R. H. Hearn, J. R. Zeidler, E. Dong Jr., R. C. Goodlin, *Proc. IEEE*, vol. 63, pp. 1692–1716, 1975.

While the above discussion has been in terms of apparatus, a method of eliminating noise associated with signals from skin-mounted physiological recording electrodes can be defined which is not apparatus dependent. To practice the method, a pair of skin-mounted physiological recording electrodes are attached to the skin of a patient with foam pads. Differential physiological signals between the recording electrodes are monitored. At least one deformation gauge is mounted on each of the foam pads of the pair of skin-mounted physiological recording electrodes. Deformation signals from the deformation gauges are monitored. An adaptive noise cancellation analysis is made of the monitored differential signals between pairs of physiological recording electrodes and the deformation signals to provide a filtered differential physiological signal. This analysis can be done by employing adaptive filtering techniques such as LMS, RLS, and Lattice algorithms. One preferred method is to employ a LMS algorithm.

BEST MODE FOR CARRYING THE INVENTION INTO PRACTICE

Figure 1:
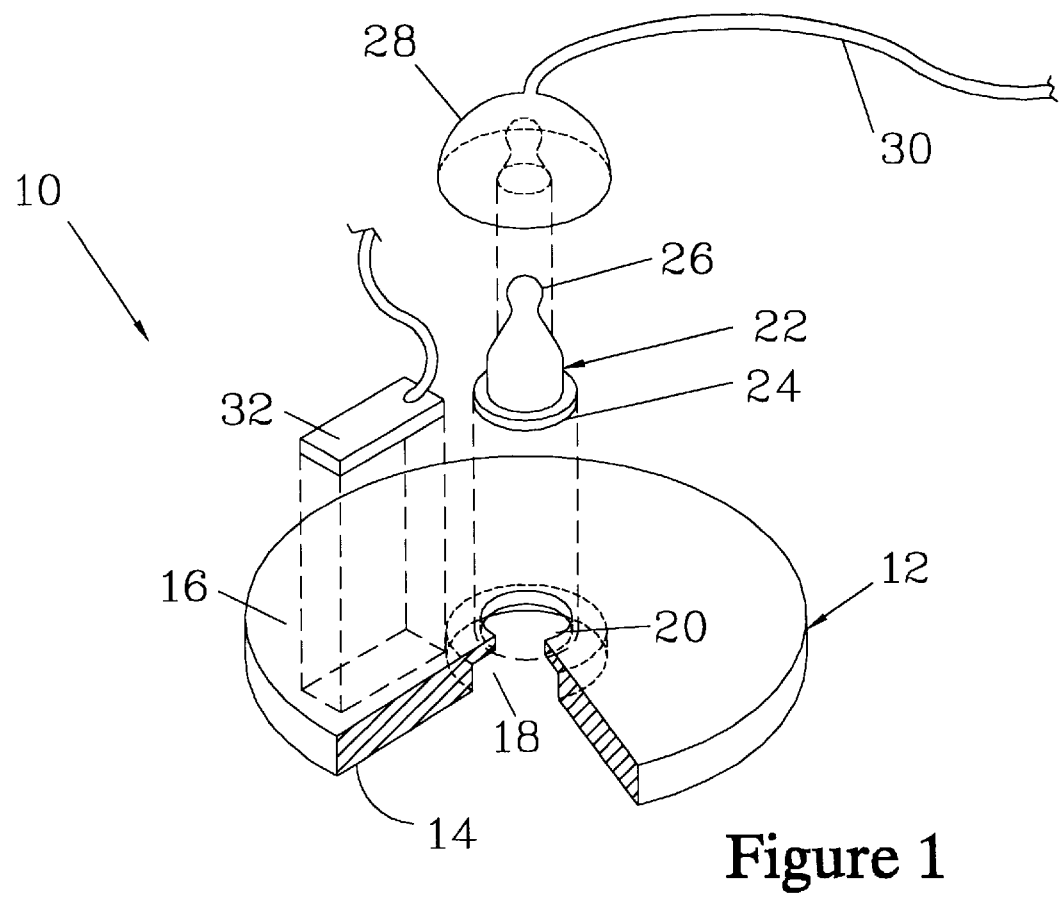
FIGS. 1 though 3 illustrate one embodiment of a skin-mounted physiological recording electrode assembly, with FIG. 1 being an exploded isometric view, FIG. 2 being an assembled isometric view, and FIG. 3 being a view of section 3—3 of FIG. 2. The electrode assembly has a foam pad having a front surface for contacting the skin and a rear surface spaced apart therefrom. The front surface of the foam pad has a central region which is recessed and a pad passage connecting the central recess to the rear surface of the foam pad. An electrode having a sensing end and a connector end is positioned in the pad passage such that the sensing end resides in the central recess of the foam pad and the connector end protrudes from the pad passage. A clip is provided which is configured to grip the connector end of the electrode. A lead wire connects the clip to remote processing and analysis equipment. A strain gauge is provided which is mounted on the rear surface of the foam pad.
Figure 2:
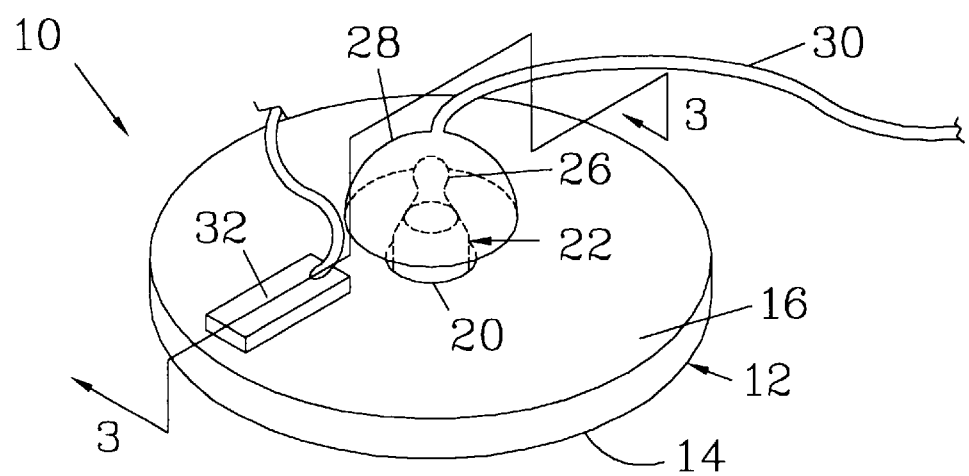
Figure 3:
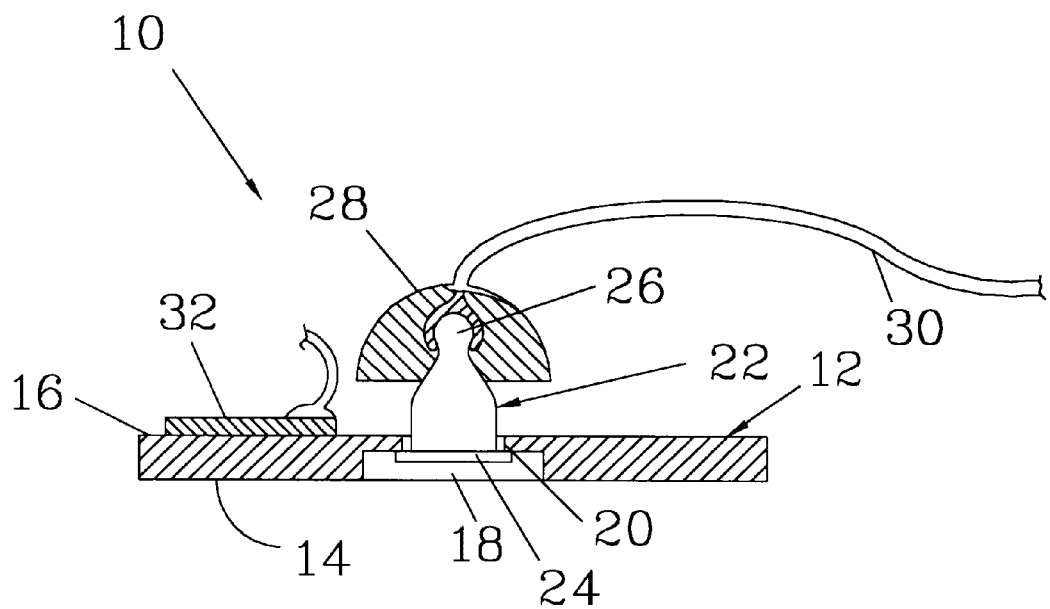

FIGS. 1 through 3 illustrate one embodiment of the present invention, a skin-mounted physiological recording electrode assembly 10. FIG. 1 shows the elements of the skin-mounted physiological recording electrode assembly 10 in exploded isometric view. FIG. 2 illustrates the elements shown in FIG. 1 in the assembled form, while FIG. 3 is a view of section 3—3 of FIG. 2. The skin-mounted physiological recording electrode assembly 10 has a foam pad 12 having a front surface 14 for adhesively mounting on the skin of a patient when testing is being conducted. The foam pad 12 terminates in a rear surface 16 which is spaced apart from the front surface 14. The front surface 14 has a central region which is recessed creating a central recess 18. A pad passage 20 communicates between the central recess 18 and the rear surface 16 of the foam pad 12.

An electrode 22, having a sensing end 24 and a connector end 26, is positioned in the pad passage 20 such that the sensing end 24 resides in the central recess 18 while the connector end 26 extends beyond the pad passage 20 and extends beyond the rear surface 16 of the foam pad 12. In use, a conductive gel or paste known in the art (not shown) is placed in the central recess 18 to provide a conductive path between the sensing end 24 of the electrode 22 and the skin of the patient.

A clip 28 is provided which can be engaged with the connector end 26 of the electrode 22 after the foam pad 12 has been attached to the skin. A lead wire 30 attaches to the clip 28 for transmitting signals to monitoring equipment. A strain gauge 32 is bonded to the rear surface 16 of the foam pad 12 and monitors the deformation in the foam pad 12 as it stretches and contracts responsive to the underlying skin onto which the foam pad 12 is mounted.

A variety of strain gauges can be employed to monitor the foam pad 12 as it stretches and contracts. When a foil strain gauge is employed, care must be taken to choose a gauge which does not have an effective modulus of elasticity so large as to mask the stretching or contraction of the foam pad 12. Since the material of the foam pad 12 is chosen to approximate the modulus of elasticity of the skin, when the modulus of elasticity of the strain gauge 32 is much greater than the modulus of elasticity of the foam pad 12, the change in strain experienced by the strain gauge 32 will be nominal and provide a minimal variation in the signal generated by the strain gauge 32. The use of strain gauges fabricated from a conductive foam such as offered by Foam Fair Industries of Aldan Pa. provides gauges where the modulus of elasticity of the strain gauge 32 can be more closely matched with the modulus of elasticity of the foam pad 12, thus reducing the difference in strain experienced between the foam pad 12 and the strain gauge 32 and providing a signal with substantial variation in response to stretch of the foam pad 12 and the underlying skin.

Figure 4:
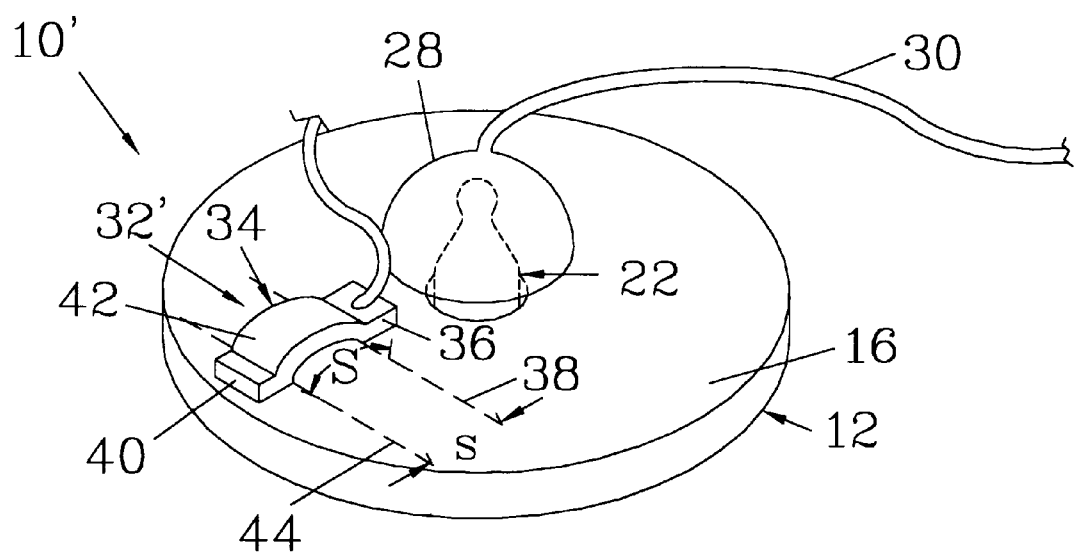
FIG. 4 illustrates an isometric view of another embodiment of a skin-mounted physiological recording electrode assembly employing a strain gauge which employs an optical bend sensor to measure skin stretch. This strain gauge is particularly effective in measuring the strain in materials having a low modulus of elasticity. The gauge employs a flexible element which is an optical bend sensing gauge. The flexible element has a first attachment region which is separated from a second attachment region by an unbonded curved region of the flexible element. The change in curvature of the curved region of the flexible element is measured to assess the resulting strain being generated in the foam pad.

FIG. 4 illustrates a skin-mounted physiological recording electrode assembly 10' which employs an alternative strain gauge 32', which has been found to be particularly well suited for incorporation into skin-mounted physiological recording electrode assemblies such as illustrated in FIGS. 1–3. The strain gauge 32' is fabricated from a bending sensor which is a fiber optic sensor 34. Fiber optic bending sensors are further described in U.S. Pat. Nos. 5,321,257 and 5,633,494. In the strain gauge 32', the fiber optic sensor 34 is affixed at a first bonded sensor region 36, which is bonded to the foam pad 12 along a first line of contact 38. A second bonded sensor region 40 is separated from the first bonded sensor region 36 by a curved unbonded sensor region 42 of length S. The second bonded sensor region 40 is bonded to the foam pad 12 along a second line of contact 44. The first line of contact 38 and the second line of contact 44 are spaced apart by a pad separation s on the foam pad 12, where the pad separation s is less than the length S of the unbonded sensor region 42, creating a curve in the curved unbonded sensor region 42. As the foam pad 12 deforms, the curvature of the curved unbonded sensor region 42 changes, which in turn changes the signal from the fiber optic circuit (not shown) associated with the fiber optic sensor 34, providing a signal that is dependant on the strain in the foam pad 12 resulting from skin stretch.

Figure 5:
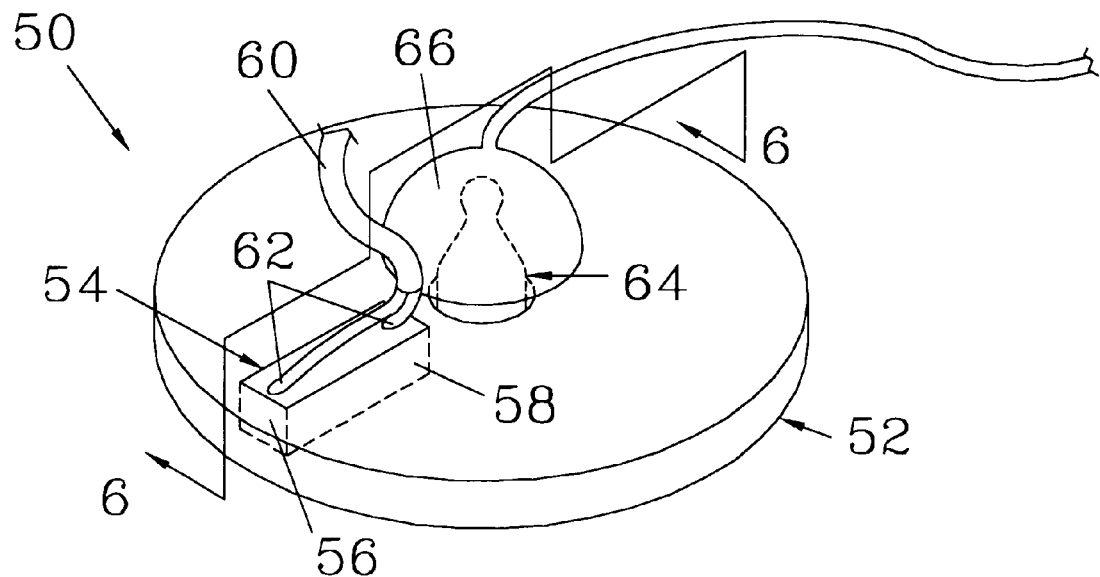
FIG. 5 is an isometric view of another embodiment of a skin-mounted physiological recording electrode assembly, employing a strain gauge which is constructed of a conductive foam and is an integral part of the foam pad.
Figure 6:
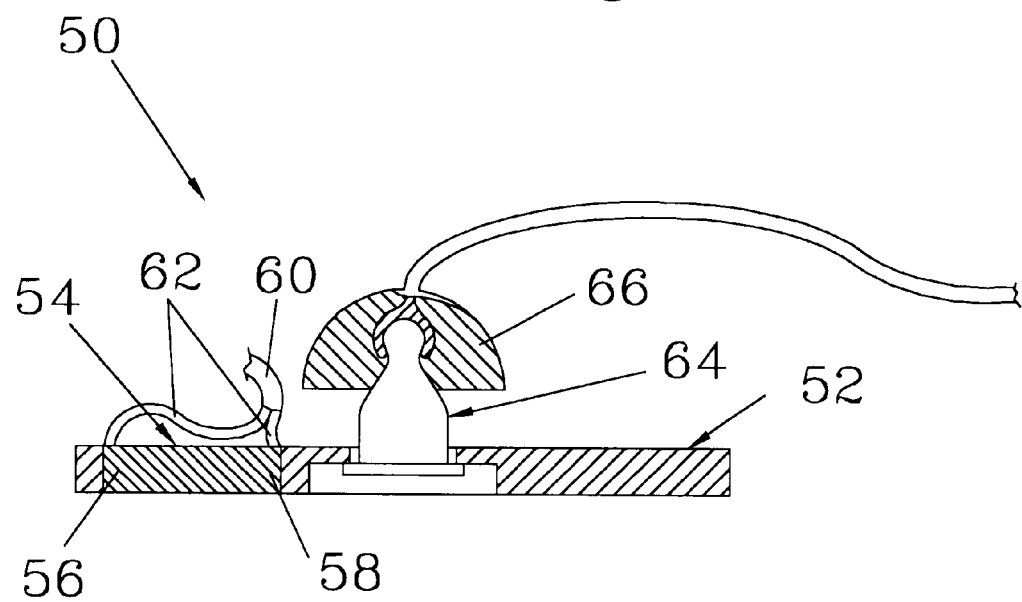
FIG. 6 is a view of section 6—6 of FIG. 5.

FIG. 5 is an isometric view of another embodiment of the present invention, a skin-mounted physiological recording electrode assembly 50. FIG. 6 is a view of the section 6—6 of FIG. 5. In this embodiment, the skin-mounted physiological recording electrode assembly 50 is similar to the embodiments discussed above and has a foam pad 52 which employs a strain gauge 54 to monitor skin stretch. The strain gauge 54 has a first strain gauge end section 56 and a second strain gauge end section 58. The strain gauge 54 is fabricated from a conductive foam and is made an integral part of the foam pad 52. A gauge lead wire 60 attaches to strain gauge leads 62, which in turn are connected to the first strain gauge end section 56 and the second strain gauge end section 58. The gauge lead wire 60 and the strain gauge leads 62 allow monitoring the change in resistance of the conductive foam of the strain gauge 54 as the conductive foam is strained due to skin stretch. As with the earlier discussed embodiments, the skin-mounted physiological recording electrode assembly 50 has an electrode 64 and a clip 66 which attaches to the electrode 64.

Figure 7:
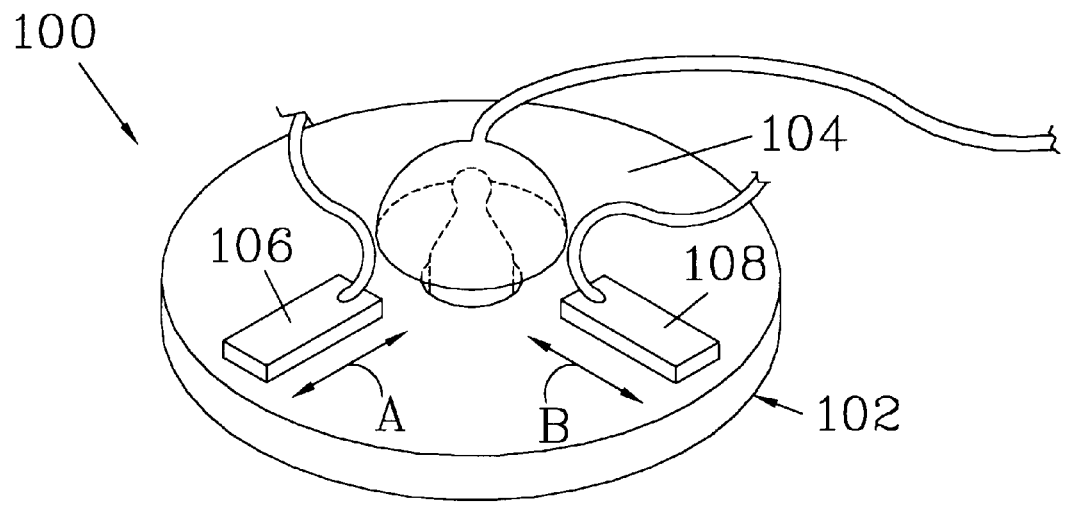
FIG. 7 illustrates another embodiment of a skin-mounted physiological recording electrode assembly which employs a first strain gauge and a second strain gauge which are attached to the rear surface of the foam pad. The second strain gauge is positioned to measure strains resulting from skin stretch which are substantially normal to the strains measured by the first strain gauge.

FIG. 7 is an isometric view of a skin-mounted physiological recording electrode assembly 100 which is similar to the embodiment shown in FIGS. 1 through 3, but which allows monitoring strains due to skin stretch in two directions. The skin-mounted physiological recording electrode assembly 100 includes the same elements as are employed in the embodiment of FIGS. 1–3, including a foam pad 102 with a rear surface 104, onto which is mounted a first strain gauge 106 which can be any of the types discussed above. The first strain gauge 106 is positioned on the foam pad 102 to measure strain in the direction indicated by the arrow A. The skin-mounted physiological recording electrode assembly 100 additionally includes a second strain gauge 108 which is also mounted on the rear surface 104 of the foam pad 102. The second strain gauge 108 is positioned with respect to the first strain gauge 106 such that it measures strain in a direction indicated by the arrow B, which is substantially normal to the direction of the arrow A that indicates the direction of strain measured by the first strain gauge 106.

The skin-mounted physiological recording electrode assemblies of FIGS. 1 through 7 have strain gauges positioned such that the signals generated by the strain gauges are responsive to the stretch of the skin. When the skin stretches as the test is conducted, it has been found that these strain gauge signals can be correlated to the noise due to motion artifact in the signal received from the electrode of the skin-mounted physiological recording electrode assembly. The signals from the strain gauges can then be processed with the signals from the electrode to reduce the noise component in the signal from the electrode.

Besides artifacts or noise resulting from the stretch of the skin, under some testing conditions there is skin normal distortion due to movement of the electrode normal to the skin. Such skin normal distortion can again result in artifacts or noise in the signal being monitored by the electrode.

Figure 8:
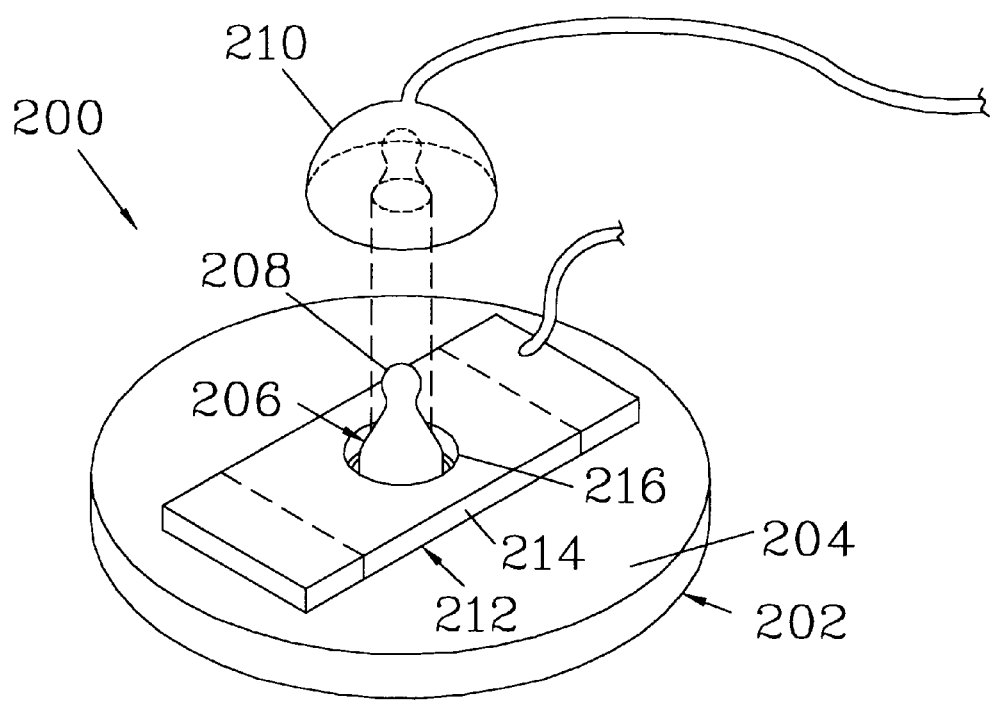
FIG. 8 is an isometric view of another embodiment of a skin-mounted physiological recording electrode assembly which employs an optical bending sensor to measure normal distortion of the foam pad which is mounted on the rear surface of the foam pad. In this embodiment the optical bending sensor is centrally mounted on the foam pad and has a central region which is adhesively bonded to the foam pad.

FIG. 8 is a partially exploded isometric view of another embodiment of the present invention, a skin-mounted physiological recording electrode assembly 200 for reducing artifacts which result from skin normal distortion. The skin-mounted physiological recording electrode assembly 200 has a foam pad 202 which is configured similarly to the foam pad 12 of the skin-mounted physiological recording electrode assembly 10 shown in FIGS. 1–3. The foam pad 202 includes a rear surface 204. As in the skin-mounted physiological recording electrode assembly 10, an electrode 206 extends beyond the rear surface 204, leaving exposed a connector end 208 of the electrode 206, onto which a clip 210 attaches. A fiber optic sensor 212, such as is described above with regard to FIG. 4, is centrally positioned on the foam pad 202 and has a central sensor region 214 of the optical sensor 212 bonded to the rear surface 204 of the foam pad 202. In this application, the bonded central sensor region 214 of the fiber optic sensor 212 is continuous rather than providing two isolated bonded regions separated by an unbonded region of the sensor. It is preferred that the electrode 206 be centrally positioned with respect to the fiber optic sensor 212. When the electrode 206 is so positioned, a sensor passage 216 is provided in the fiber optic sensor 212 to accommodate the electrode 206.

Figure 9:
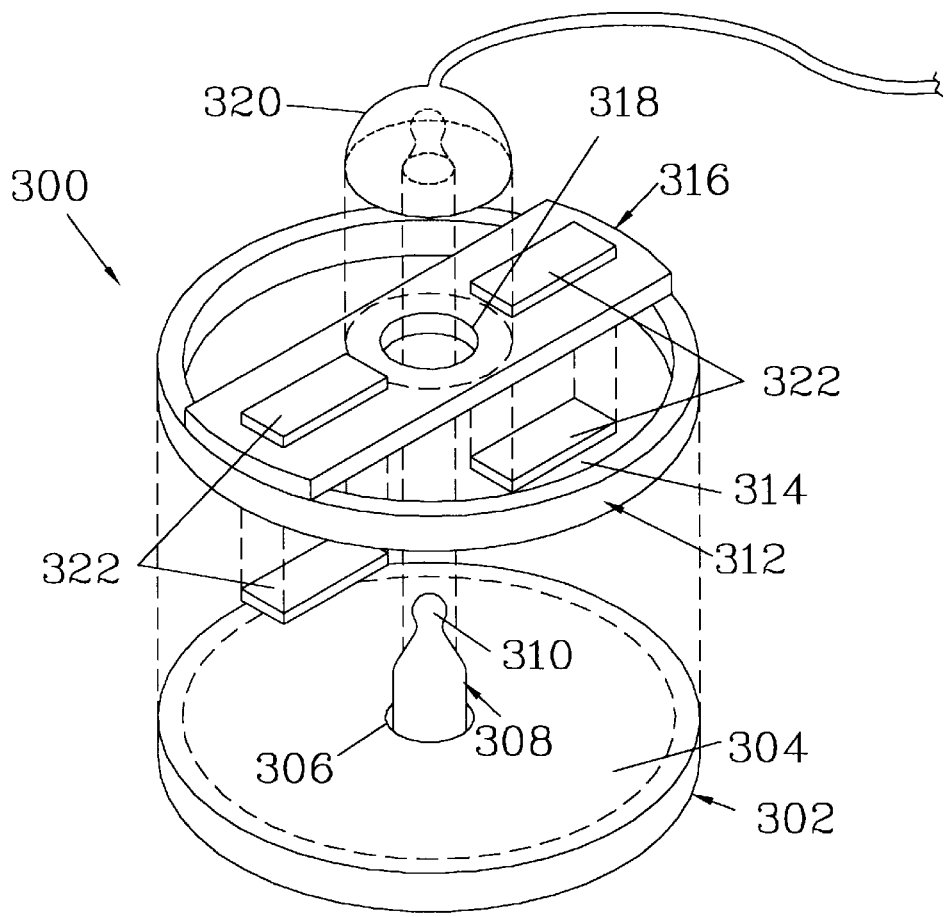
FIG. 9 is an isometric view of another embodiment of a skin-mounted physiological recording electrode assembly which employs a resilient strip which serves as a mechanical bend-sensing gauge. The resilient strip is mounted on a frame which in turn rests on the rear surface of the foam pad. In this embodiment, the resilient strip has a strip passage through which the electrode passes. A clip is provided which, when connected to the electrode, presses on the resilient strip and forcibly engages the frame with the foam pad and minimizes motion therebetween. Up to four strain gauges are pairwise attached to the resilient strip to measure the change in curvature in the resilient strip which occurs as the foam pad deforms.

FIG. 9 is an exploded isometric view of a skin-mounted physiological recording electrode assembly 300 which is functionally equivalent to the skin-mounted physiological recording electrode assembly 200 illustrated in FIG. 8, but which does not require affixing the bending sensor elements to a foam pad 302, facilitating reuse of the bending sensor elements. The foam pad 302 is configured similarly to the foam pad 12 of the skin-mounted physiological recording electrode assembly 10 of FIGS. 1–3. The foam pad 302 includes a rear surface 304 having a pad passage 306 through which an electrode 308 passes, leaving a connector end 310 exposed and spaced apart from the rear surface 304 of the foam pad 302.

A ring 312 is provided which serves as a frame having a central opening 314. When the skin-mounted physiological recording electrode assembly 300 is assembled, the ring 312 mounts on the rear surface 304 of the foam pad 302. A resilient strip 316 spans the ring 312 and attaches thereto. The resilient strip 316 has a strip passage 318 through which the electrode 308 passes. The ring 312 and resilient strip 316 are so configured that, when a clip 320 is engaged with the connector end 310 of the electrode 308, the clip 320 results in a slight bending of the resilient strip 316 toward the rear surface 304 of the foam pad 302. This bending of the resilient strip 316 maintains the ring 312 forcibly engaged with the rear surface 304 of the foam pad 302 and minimizes motion therebetween.

As the electrode 308 moves normal to the skin, the resilient strip 316 will deflect. This deflection can be measured by one or more strain gauges 322 to generate a signal which is correlated to the deflection of the resilient strip 316, which in turn is proportional to the displacement: of the electrode 308 from the skin. The embodiment shown in FIG. 9 has four strain gauges 322 arranged in pairs, each pair having one of the strain gauges 322 on opposed sides of the resilient strip 316. For maximum sensitivity, the four strain gauges 322 are typically wired to form a Wheatstone bridge.

Figure 10:
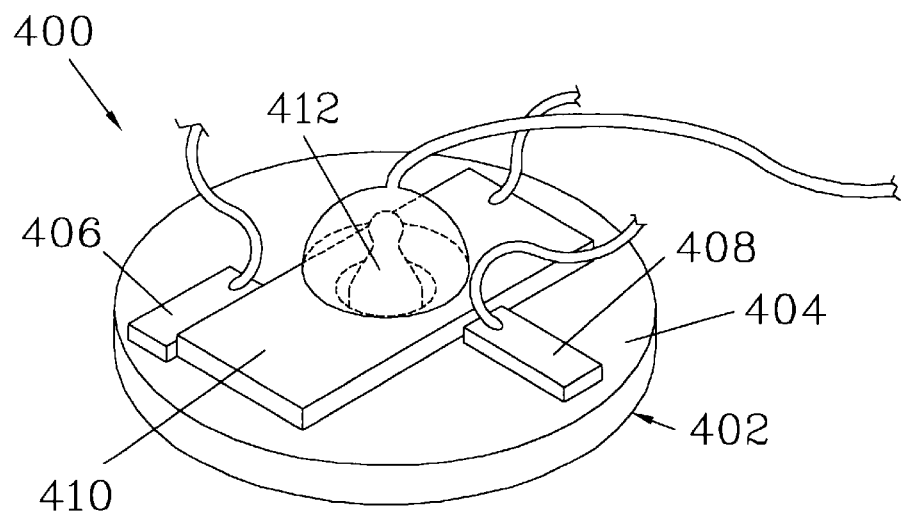
FIG. 10 is an isometric view of another embodiment of a skin-mounted physiological recording electrode assembly which employs three deformation gauges. A first strain gauge and a second strain gauge are mounted on the foam pad and arranged such that the first strain gauge will measure strains which are substantially normal to the strains measured by the second strain gauge. The third deformation gauge is an optical bending sensor which is centrally mounted on the foam pad.

FIG. 10 is an isometric view a skin-mounted physiological recording electrode assembly 400 of an embodiment which provides signals which are responsive to both skin stretch and to skin normal distortion. The skin-mounted physiological recording electrode assembly 400 has a foam pad 402 which is configured similarly to the foam pads discussed above and which has a rear surface 404. A first strain gauge 406 and a second strain gauge 408 are both bonded to the rear surface 404 of the foam pad 402. The first strain gauge 406 and the second strain gauge 408 are positioned substantially normal to each other and the pair of gauges (406 and 408) so positioned reduce the angular dependence of the strain field relative to the strain gauges (406 and 408). A fiber optic bending sensor 410 is also bonded to the rear surface 404 of the foam pad 402 to monitor pad normal distortion of the foam pad 402 and the skin normal distortion of the underlying skin. With the skin-mounted physiological recording assembly 400, signals responsive to both skin stretching and movement of an electrode 412 normal to the skin are generated, and these signals can be used to analyze noise in the signals received from the electrode.

Figure 11:
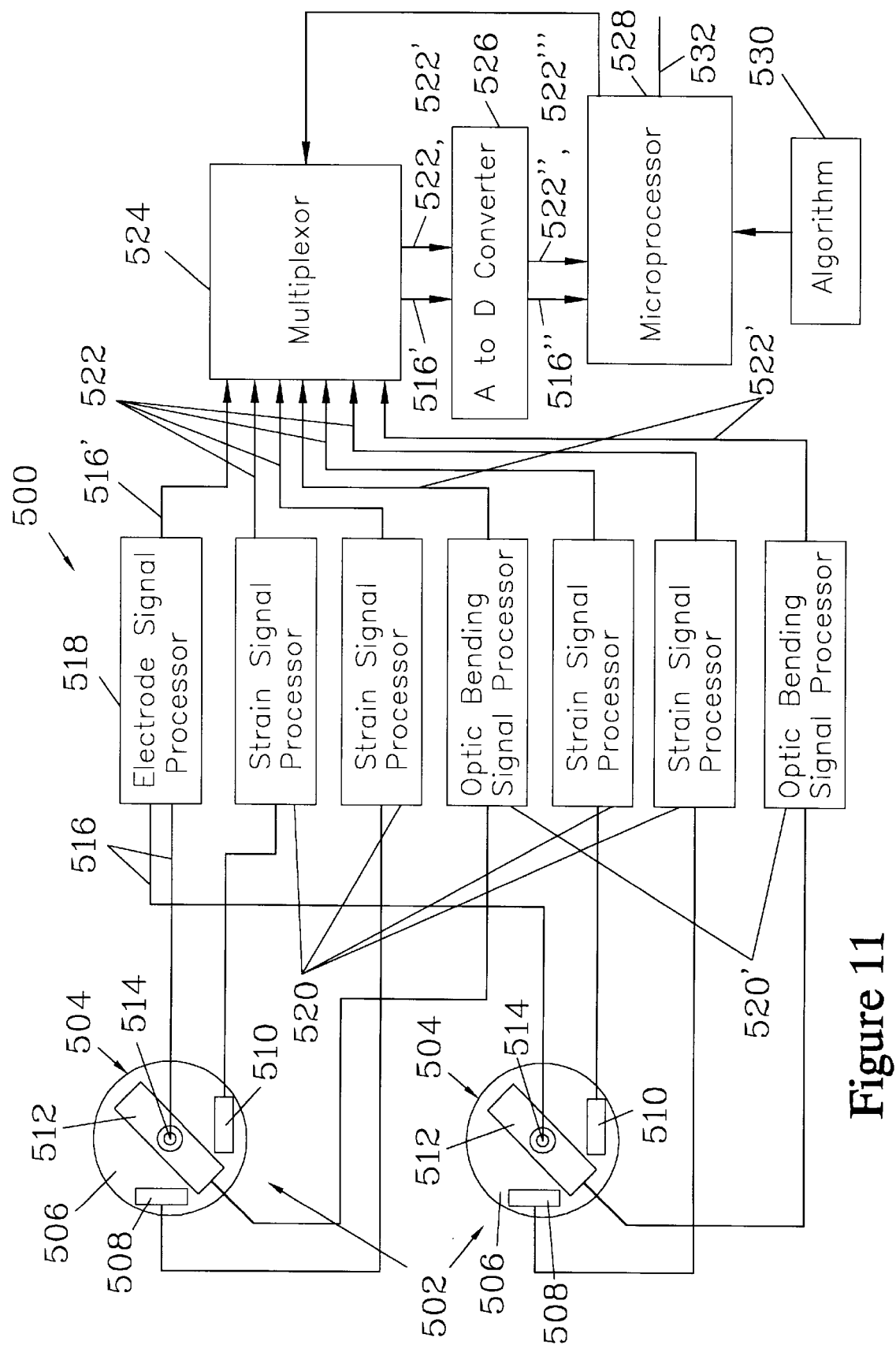
FIG. 11 illustrates a patient monitoring system which employs a pair of skin-mounted physiological recording electrode assemblies such as shown in FIGS. 1 through 10.

The above described skin-mounted physiological recording electrode assemblies have particular utility when they are integrated into a patient monitoring system 500, such as is illustrated in FIG. 11. The patient monitoring system 500 includes paired skin-mounted physiological recording electrode assemblies 502. In the patient monitoring system 500 illustrated, one pair of skin-mounted physiological recording electrode assemblies 502 is illustrated, which is the minimum number needed to obtain sufficient physiological data for an analysis which is based on pairwise differences in the physiological signals received from the individual electrode assemblies 502.

Each of the skin-mounted physiological recording electrode assemblies 502 of this embodiment are substantially the same as the skin-mounted physiological recording electrode assembly 400 illustrated in FIG. 10. It should be appreciated that other embodiments of skin-mounted physiological recording electrode assemblies, such as illustrated and discussed above, could be substituted in the patient monitoring system 500. The skin-mounted physiological recording electrode assemblies 502 illustrated each have a foam pad 504 having a rear surface 506. A first strain gauge 508 and a second strain gauge 510 are affixed to the rear surface 506 of each foam pad 504. Each foam pad 504 also has a fiber optic sensor 512, which serves as an optical bending sensor, affixed to the rear surface 506 of the foam pad 504.

Each skin-mounted physiological recording electrode assembly 502 also has an electrode 514 for transmitting a physiological signal 516 of the patient. While the patient monitoring system 500 can be utilized for the monitoring of various types of signals such as ECG, EMG, and EEG signals, the discussion will be terms of monitoring ECG signals. In this example, each electrode 514 provides a local skin potential which serves as the physiological signal 516. The physiological signal 516 may have associated with it a motion artifact component resulting from deformation of the skin at the electrodes 514. The deformation of the skin, as discussed above, can result from skin stretch as well as skin normal distortion which can be caused by applying pressure to the electrode 514.

The patient monitoring system 500 has an electrode signal processor 518 which receives the physiological signals 516 from each of the electrodes 514 of the at least one pair of physiological recording electrode assemblies 502 and generates an amplified differential physiological signal 516' which, in the example illustrated, provides an ECG signal.

While only a single electrode signal processor 518 is illustrated, it should be noted that additional electrode signal processors 518 are employed when there are additional physiological recording electrode assemblies 502. Each electrode signal processor 518 is associated with a pair of physiological recording electrode assemblies 502. It should be noted that the pairs may overlap, rather than being discrete. Thus, three physiological recording electrode assemblies 502 could be divided into three pairs, each of which would provide physiological signals 516 to an associated electrode signal processor 518. Alternatively, the same three physiological recording electrode assemblies 502 could be divided into only two pairs, with the signal corresponding to the third pair being later calculated from the difference between the two pairs in the manner known in the art. In all cases, the electrode signal processor 518 provides an amplified differential physiological signal 516' from the physiological signals 516 received from its associated pair of physiological recording electrode assemblies 502.

Deformation signal processors (520, 520') are also provided, which are connected to each of the deformation gauges (508, 510, and 512) to provide processed deformation signals (522, 522'). These deformation signal processors (520, 520') are of two types, strain signal processors 520 and optical bending signal processors 520'. The strain signal processors 520 provide processed strain signals 522 which are responsive to the strain experienced by the strain gauges (508, 510) due to skin stretch and which have been amplified to an appropriate level. Similarly, the optical bending signal processors 520' provide processed skin normal distortion signals 522' which are responsive to the bending of the fiber optic bending sensors 512 due to skin normal distortion.

A multiplexer 524 is provided which selectively passes the amplified differential physiological signals 516' and the processed deformation signals (522, 522') to an A-to-D convertor 526. The A-to-D convertor 526 digitizes the amplified differential physiological signals 516' and the processed deformation signals (522, 522') received to provide respectively digital differential physiological signals 516" and digital deformation signals (522", 522'").

A microprocessor 528 is provided which controls the selectivity of the multiplexer 524 and receives the digital signals (516", 522", 522'") provided by the A-to-D converter 526. The microprocessor 528 is programmed with an adaptive noise canceling algorithm 530 for instructing the microprocessor 528 to combine the digital differential physiological signals 516" and the digital deformation signals (522", 522'") to provide filtered digital physiological signals 532. The filtered digital physiological signal 532 for each pair of physiological recording electrode assemblies 502 corresponds to the amplified differential physiological signal 516' for that pair of physiological recording electrode assemblies 502, but where the motion artifact component of the physiological signals 516 resulting from deformation of the skin at the electrodes 514 has been reduced or eliminated.

Further discussion of adaptive filter algorithms which can be applied for use as adaptive noise canceling algorithms is found in *Advanced Digital Signal Processing* by Proakis, Rader, Ling, Nikias (Macmillan Publishing, New York, 1992) and is described in a paper entitled: "Adaptive Noise Canceling: Principals and Applications", B. Widrow, J. R. Glover Jr., J. M. McCool, J. Kaunitz, C. S. Williams, R. H. Hearn, J. R. Zeidler, E. Dong Jr., R. C. Goodlin, *Proc. IEEE*, vol. 63, pp. 1692–1716, 1975. Source code is provided in Appendix A for a LMS algorithm which treats signals from a pair of electrode assemblies, each having a single deformation gauge.

While the above discussion has been in terms of apparatus, a method of eliminating noise associated with readings from skin-mounted physiological recording electrodes can be defined which is not apparatus dependent. The method employs the following steps.

A pair of skin-mounted physiological recording electrodes are attached to the skin of a patient with foam pads. Physiological signals are received from the electrodes and are monitored. These physiological signals are processed to provide a differential physiological signal which is defined by the difference between the physiological signals received from the recording electrodes.

At least one deformation gauge is mounted on each of the foam pads of the pair of skin-mounted physiological recording electrodes. Deformation signals, which correlate to the deformation of the deformation gauges, are monitored. The deformation gauges are selected such that the deformation of the deformation gauges is correlated to the deformation of the foam pads and the underlying skin.

An adaptive noise cancellation analysis is performed on the monitored differential signals between pairs of physiological recording electrodes using the deformation signals to provide a filtered differential physiological signal. For simplicity, it is preferred to employ a least means squared-based (LMS) adaptive noise cancellation analysis.

In a preferred method, the deformation signals are responsive to the combined strain of two strain gauges which are each positioned to monitor strains which are normal to the strains measured by the other, thus providing an effective strain due to skin stretch in the foam pads. It is further preferred for the deformation signals to be correlated to the effective skin stretch in the foam pads which is combined with the normal distortion of the foam pads.

While the novel features of the present invention have been described in terms of particular embodiments and preferred applications, it should be appreciated by one skilled in the art that substitution of materials and modification of details obviously can be made without departing from the spirit of the invention.

Appendix A

```
//////////////////////////////////////////////////////////////////////
// LMSFilter implements an LMS adaptive noise removal
// filter. The reference signal is assumed to be in
// data[0] and the signal and noise are assumed
// to be in data[1].
//////////////////////////////////////////////////////////////////////
#include <math.h>
#define FilterOrder 2
// #define beta 2e-7
#define SubSample 6
#define LMSBufferLength FilterOrder*SubSample
void LPF(int *data) ;
double GetBeta(int *data, double a, int init) ;
double LMSBuffer [LMSBufferLength] ;
double LMSCoefficients [FilterOrder] ;
int LMSFilter(int *data, double a, int init)
   {
   double estimate, error, beta
   int i ;
   if(init != 0)
      {
      for (i=0; i < FilterOrder; ++i)
         LMSCoefficients[i] = 0 ;
      for (i = 0; i < FilterOrder*2; ++i)
         LMSBuffer[i]=0 ;
      GetBeta (data, a, 1) ;
      return 0 ;
      }
   beta = GetBeta(data,a,0) ;
// for(i = 0; i < 3; ++i)
//     data[i] = input[i] ;
   // Filter the data.
// LPF(data) ;
   // Shift Buffer Elements.
   for(i=(LMSBufferLength)-2; i >= 0; --i)
```

Appendix A-continued

```
      LMSBuffer[i+1]= LMSBuffer[i] ;
   LMSBuffer[0] = data[0] ;
   for(estimate = 0, i = 0; i < FilterOrder; ++i)
      estimate += LMSCoefficients[i] * LMSBuffer[i*SubSample] ;
   error = (double) data[1] - estimate ;
   // Update coefficients.
     for(i = 0; i < FilterOrder; ++i)
        LMSCoefficients[i] =
           LMSCoefficients[i] +
           beta * LMSBuffer[i*SubSample] * error ;
// error = (double) data[2] - estimate ;
// input[1] = data[2] ;
   return((int) error) ;
   }
#define LPFLength (SubSample*2+1)
void LPF(int *data)
   {
   static int LPFBuffer[2] [LPFLength], LPFBPtr = 0 ;
   static long LPFSums[2]={0,0} ;
   int tempPtr, i ;
   // Filter the first two channels.
   for (i = 0; i < 2; ++i)
      {
      LPFSums[i] -= LFBuffer[i] [LPFBPtr] ;
      LPFSums[i] += data[i] ;
      LPFBuffer[i] [LPFBPtr] = data[i] ;
      data[i] = LPFSums[i]/LPFLength ;
      }
   tempPtr = LPFBPtr-(LPFLength>>1) ;
   if(tempPtr < 0)
      tempPtr += LPFLength ;
   // The third channel is simply a
   // delayed version of the second channel.
   data[2] = LPFBuffer[1] [tempPtr] ;
   if(++LPFBPtr == LPFLength)
      LPFBPtr = 0 ;
   }
#define DelayLength 200
double GetBeta(int *data, double a, int init)
   {
   static int dataDelay[2] [DelayLength], delayPtr = 0 ;
   static double SquaredSum ;
   double temp, varEst, b ;
   int tempPtr ;
   if (init)
      {
      SquaredSum = 0 ;
      for(delayPtr = 0; delayPtr < DelayLength; ++delayPtr)
         dataDelay[0] [delayPtr] = dataDelay[1] [delayPtr] = 0 ;
      delayPtr = 0 ;
      return 0 ;
      }
   // Update variance estimate.
   temp = dataDelay[0] [delayPtr] ;
   temp *= dataDelay[1] [delayPtr] ;
   SquaredSum -= abs(temp) ;
   temp = data[0] ;
   temp *= data[1] ;
   SquaredSum += abs(temp) ;
   varEst = SquaredSum/DelayLength ;
   // Delay the data.
   dataDelay[0] [delayPtr] = data[0] ;
   dataDelay[1] [delayPtr] = data[1] ;
   tempPtr = delayPtr - (DelayLength/2) ;
   if (tempPtr < 0)
      tempPtr += DelayLength ;
   data[0] = dataDelay[0] [tempPtr] ;
   data[1] = dataDelay[1] [tempPtr] ;
   // Update the delay line pointer.
   if(++delayPtr == DelayLength)
      delayPtr = 0 ;
   b = a/(varEst + 1) ;
   return (b) ;
   }
/* double GetBeta(int d, int s, int init)
   {
   static double varEst= 2e6 ;
   double dd, ds, b ;
   if(init != 0)
```

Appendix A-continued

```
    varEst = 2e6 ;
  if(abs(d) > 30)
    {
    dd = d ;
    ds = s ;
    varEst = 0.95*varEst + 0.05*abs(ds*dd) ;
    }
  b = 9e-3/(varEst + 1) ;
  return(b) ;
  }
*/
```

What we claim is:

1. An improved skin-mounted physiological recording electrode assembly for use with a recording instrument, the improved skin-mounted physiological recording electrode assembly having,
  a foam pad having a front surface, for adhesively mounting to, complying with and conforming to the skin as the skin deforms, and a rear surface,
    the foam pad having a central region which is recessed on the front surface, forming a central recess, and
    the foam pad also having a pad passage connecting the central recess to the rear surface of the foam pad,
  an electrode having a sensing end and a connector end,
    the electrode being positioned in the pad passage such that the sensing end resides in the central recess while the connector end extends beyond the pad passage and beyond the rear surface of the foam pad,
  a clip attaching to the connector end of the electrode, and
  a lead wire connected to the clip for connection to a patient monitoring device,
the improvement comprising:
  at least one deformation gauge coupled to the foam pad so as to be responsive to deformation experienced by the foam pad.

2. The improved skin-mounted physiological recording electrode assembly of claim 1 wherein said at least one deformation gauge is a first strain gauge attached to the rear surface of the foam pad.

3. The improved skin-mounted physiological recording electrode assembly of claim 2 wherein said first strain gauge is a resistance strain gauge.

4. The improved skin-mounted physiological recording electrode assembly of claim 3 further comprising:
  a second resistance strain gauge attached to the rear surface of the foam pad and so positioned as to measure strains which are substantially normal to the strains measured by said first strain gauge.

5. The improved skin-mounted physiological recording electrode assembly of claim 2 wherein said first strain gauge further comprises:
  a first flexible element having a first element first attachment region separated from a first element second attachment region, by a first element curved unbonded region of length S,
    said first element first attachment region and said first element second attachment region being attached to the foam pad at locations separated by a pad separation s which is less than said length S; and
  means for sensing the change in curvature of said first element curved unbonded region.

6. The improved skin-mounted physiological recording electrode assembly of claim 5 wherein said first flexible element is a first optical bending sensor.

7. The improved skin-mounted physiological recording electrode assembly of claim 6 further comprising:
  a second strain gauge having,
    a second flexible element which is a second optical bending sensor having a second element first attachment region separated from a second element second attachment region by a second element curved unbonded region of length S2,
      said second element first attachment region and said second element second attachment region being attached to the foam pad at locations separated by a second pad separation s2 which is less than said length S2, and
    means for sensing the change in curvature of said second element curved unbonded region,
      said second strain gauge being so positioned as to measure strains which are substantially normal to the strains measured by said first strain gauge.

8. The improved skin-mounted physiological recording electrode assembly of claim 2 further comprising:
  a second strain gauge attached to the rear surface of the foam pad and so positioned as to measure strains which are substantially normal to the strains measured by said first strain gauge.

9. The improved skin-mounted physiological recording electrode assembly of claim 2 wherein said first strain gauge is a foam strain gauge.

10. The improved skin-mounted physiological recording electrode assembly of claim 9 further comprising:
  a second foam strain gauge attached to the rear surface of the foam pad and so positioned as to measure strains which are substantially normal to the strains measured by said first strain gauge.

11. The improved skin-mounted physiological recording electrode assembly of claim 1 wherein said at least one deformation gauge is a first strain gauge embedded in the foam pad.

12. The improved skin-mounted physiological recording electrode assembly of claim 1 wherein said at least one deformation gauge is a bending sensor centrally mounted on the foam pad such that it bends responsive to normal distortion of the foam pad.

13. The improved skin-mounted physiological recording electrode assembly of claim 12 wherein said bending sensor is an optical bending sensor having a central region coupled to the foam pad.

14. The improved skin-mounted physiological recording electrode assembly of claim 12 further comprising:
  a first strain gauge attached to the rear surface of the foam pad.

15. The improved skin-mounted physiological recording electrode assembly of claim 14 further comprising:
  a second strain gauge attached to the rear surface of the foam pad and so positioned as to measure strains which are substantially normal to the strains measured by said first strain gauge.

16. The improved skin-mounted physiological recording electrode assembly of claim 15 wherein said bending sensor is an optical bending sensor which is bonded to the foam pad.

17. The improved skin-mounted physiological recording electrode assembly of claim 1 wherein the foam pad terminates in a peripheral region and further wherein said at least one deformation gauge is a bending sensor which further comprises:
  a frame having a central open region, said frame being configured to engage the peripheral region of the foam pad;

a resilient strip having a strip passage therethrough, said resilient strip attaching to said frame arid spanning said central open region;

at least one strain gauge attached to said resilient strip; and means for bending said resilient strip when the clip is engaged with the connector end of the electrode, thereby forcibly engaging said frame with the foam pad and minimizing motion therebetween.

18. The improved skin-mounted physiological recording electrode assembly of claim 17 wherein said resilient strip has a strip top surface and a strip bottom surface, and said at least one strain gauge further comprises:

a first strain gauge mounted to said strip top surface of said resilient strip;

a second strain gauge, said second strain gauge being mounted to said strip bottom surface of said resilient strip and positioned opposite said first strain gauge;

a third strain gauge, said third strain gauge being mounted to said strip top surface of said resilient strip and positioned with respect to said strip passage so as to be opposed to said first strain gauge;

a fourth strain gauge, said fourth strain gauge being mounted to said strip bottom surface of said resilient strip and positioned opposite said third strain gauge.

19. The improved skin-mounted physiological recording electrode assembly of claim 1 wherein said at least one deformation gauge is a first foam strain gauge embedded in the foam pad.

20. A patient monitoring system comprising:

at least one pair of physiological recording electrode assemblies, each physiological recording electrode assembly of said at least one pair of physiological recording electrode assemblies having, a foam pad having a front surface for contacting the skin and a rear surface, said foam pad having a central region which is recessed on said front surface forming a central recess, a pad passage connecting said central recess to said rear surface of said foam pad, an electrode which transmits physiological signals, said electrode having a sensing end and a connector end, said electrode residing in said pad passage such that said sensing end resides in said central recess while said connector end protrudes from said pad passage, a clip attaching to said connector end of said electrode, a lead wire connected to said clip, at least one deformation gauge for providing deformation signals, said at least one deformation gauge being coupled to said foam pad;

an electrode signal processor for each of said at least one pair of physiological recording electrode assemblies, said electrode signal processor being connected to said lead wires of said physiological recording electrode assemblies for receiving said physiological signals and providing amplified differential physiological signals;

a deformation signal processor for each of said at least one deformation gauges, said deformation signal processor generating processed deformation signals from said deformation signals;

a multiplexor for selectively passing said amplified differential physiological signals and said processed deformation signals;

an A-to-D Converter for digitizing said amplified differential physiological signals and said processed deformation signals providing digital differential physiological signals and digital deformation signals;

a microprocessor for receipt of said digital differential physiological signals and said digital deformation signals; and an adaptive noise canceling algorithm for instructing said microprocessor to combine said digital differential physiological signals and said digital deformation signals to provide filtered digital physiological signals.

21. The patient monitoring system of claim 20 wherein said at least one deformation gauge for providing deformation signals further comprises:

a first strain gauge attached to said rear surface of said foam pad; and a normal distortion gauge attached to said rear surface of said foam pad.

22. The patient monitoring system of claim 21 wherein said at least one deformation gauge for providing said deformation signals further comprises:

a second strain gauge attached to said rear surface of said foam pad and so positioned as to measure strains which are substantially normal to strains measured by said first strain gauge.

23. A method for increasing the reliability of signals from skin-mounted physiological recording electrodes mounted to the skin of a patient, the method comprising the steps of:

attaching a pair of skin-mounted physiological recording electrodes to the skin with foam pads;

monitoring physiological signals received from said pair of physiological recording electrodes;

calculating a differential physiological signal which is defined as the difference between said physiological signals from said pair of physiological recording electrodes;

mounting at least one deformation gauge on each of said foam pads;

monitoring deformation signals which are correlated to the deformation of said at least one deformation gauge; and performing an adaptive noise cancellation on said differential physiological signal using said deformation signals to provide a noise-free differential signal.

24. The method of claim 23 wherein said deformation signals are correlated to strain in said foam pads due to skin stretch.

25. The method of claim 23 wherein said deformation signals are correlated to strain in said foam pads due to skin stretch in combination with normal distortion of said foam pads due to skin normal distortion.

* * * * *